United States Patent [19]

Akselrod et al.

[11] Patent Number: 4,945,917
[45] Date of Patent: Aug. 7, 1990

[54] METHOD AND APPARATUS FOR INDICATING REPETITION INTERVALS OF A SPECIFIED COMPONENT OF A COMPOSITE ELECTRICAL SIGNAL, PARTICLARLY USEFUL FOR DISPLAYING FETAL R-WAVES

[76] Inventors: Solange Akselrod, 18 Rahayat Ilan, Givat Shmuel; Jacob Karin, 24 Lean Street, Ramat-Gan; Michael Hirsch, 37 Nordau Street, Herzliya, all of Israel

[21] Appl. No.: 197,190

[22] Filed: May 23, 1988

[30] Foreign Application Priority Data

May 29, 1987 [IL] Israel .......................................... 82698

[51] Int. Cl.[5] .............................................. A61B 5/04
[52] U.S. Cl. ..................................... 128/696; 128/698; 128/706; 128/710
[58] Field of Search ................... 324/78 R, 78 Z, 162; 128/705, 696, 698, 702, 703, 706, 710, 695

[56] References Cited

U.S. PATENT DOCUMENTS

| | | | |
|---|---|---|---|
| 3,594,555 | 9/1968 | Klein et al. | 324/162 |
| 4,393,877 | 7/1983 | Imran et al. | 128/705 |
| 4,537,200 | 8/1985 | Widrow | 128/696 |
| 4,704,681 | 11/1987 | Shimizu et al. | 128/706 |
| 4,781,200 | 11/1988 | Baker | 128/698 |

Primary Examiner—Francis Jaworski
Assistant Examiner—George Manuel
Attorney, Agent, or Firm—Benjamin J. Barish

[57] ABSTRACT

The method and apparatus particularly are applicable for displaying the fetal R-wave with respect to the maternal R-wave, and comprise the steps of generating a first electrical signal corresponding to the second derivative of the composite signal (maternal R-wave); generating a second electrical signal corresponding to the second derivative of the composite signal after the specified component has been removed; subtracting the second electrical signal from the first electrical signal to produce a third electrical signal; and utilizing the third electrical signal for indicating the repetition intervals (fetal R-waves) of the specified component.

20 Claims, 13 Drawing Sheets

METHOD AND APPARATUS FOR INDICATING REPETITION INTERVALS OF A SPECIFIED COMPONENT OF A COMPOSITE ELECTRICAL SIGNAL, PARTICLARLY USEFUL FOR DISPLAYING FETAL R-WAVES

BACKGROUND OF THE INVENTION

The present invention relates to a method and apparatus for indicating the repetition intervals of a specified component of a composite, cyclically-repeating electrical signal. The invention is particularly applicable for displaying the fetal R-wave with respect to the maternal R-wave, and therefore is described below with respect to this application, although it will be appreciated that the invention can be used in other applications as well.

It has been generally recognized that whereas the fetal ECG (electrocardiographic) signals can sometimes be picked up at the mother's abdominal surface even earlier than about 20 weeks of gestation, measurement and analysis of the fetal component in the abdominal recording is a complex problem. There are several reasons for this:

(1) Electrical signals from the fetal heart, when measured at the mother's abdominal surface, are very low in amplitude, often less than 10 $\mu$V. They may be weaker than myoelectric signals produced by movement of the mother, particularly during labor.

(2) The strongest signal picked up at the maternal abdominal surface is the maternal electrocardiogram, which may be anywhere from 5 to 1000 times higher in amplitude than the fetal signal. This signal must be removed or otherwise taken into account if the abdominal ECG is to be used for reliable assessment of the fetal ECG.

(3) There is no commonly agreed answer to the question whether the medium of electrical conduction (of fetal signals to maternal abdominal electrodes) should be considered even approximately homogeneous, and there are indications that this pattern of conduction may vary over gestation. This complicates the analysis of the fetal electrocardiogram even when it can be measured. Further the appearance of the vernix covering the fetal skin during the last three months of fetal life, introduces a high electrical impedance between the source of fetal electrocardiographic signals and the measuring electrodes. This can substantially reduce the amplitude of the fetal electrocardiogram as it is measured on the maternal abdominal surfaces. This is probably one of the reasons why the quality of abdominally obtained fetal ECG's deteriorates in the period between about 26 and 33 weeks of gestation.

(4) Fetal position in-utero varies with time and varies among patients. The location of the site of placentation (which may be at least partly responsible for the electrical conduction of fetal heart signals to the mother's abdominal surface) also varies among patients. Therefore, even if the fetal electrocardiogram can be obtained from the maternal abdomen, standardizing it is a much more complex matter than in case of adult electrocardiograms.

Reliable, non-invasive observation of the fetal ECG in abdominal recordings is of significant diagnostic importance in the monitoring of pregnancies, not only for fetal heart rate assessment, but also for observation of congenital cardiac malformations and transient difficulties before and during labor. Furthermore, a reliable abdominally obtained fetal electrocardiogram may be used to assess fetal heart rate variability in the antepartum period of gestation when it is not possible to obtain a fetal scalp lead electrocardiogram.

One approach for indicating the repetition intervals of the fetal R-waves is merely to remove the maternal R-waves from the abdominal ECG signal (which includes both the maternal R-waves and the fetal R-waves), thereby leaving only the fetal R-waves. However, such a system is very sensitive to baseline changes originated by body movements; moreover, it cannot detect a fetal R-wave falling on a maternal R-wave. A number of other techniques have been proposed for indicating the repetition intervals of the fetal R-waves, but none has been proved to be entirely satisfactory because of the difficulties discussed above.

An object of the present invention is to provide a novel method, and also novel apparatus, for indicating the repetition intervals of a specified component of a composite, cyclically-repeating electrical signal, which method and apparatus are particularly useful for indicating the fetal R-waves.

BRIEF SUMMARY OF THE INVENTION

According to a broad aspect of the present invention, there is provided a method of indicating the repetition intervals of a specified component of a composite cyclically-repeating electrical signal, comprising the steps: generating a first electrical signal corresponding to the second derivative of the composite signal; generating a second electrical signal corresponding to the second derivative of the composite signal after the specified component has been removed; subtracting the second electrical signal from the first electrical signal to produce a third electrical signal; and utilizing the third electrical signal for indicating the repetition intervals of the specified component.

Preferably, the last step is performed by generating a fourth electrical signal corresponding to the first derivative of the composite signal, generating a fifth electrical signal corresponding to the first derivative of the composite signal after the specified component has been removed, subtracting the fifth electrical signal from the fourth electrical signal to produce a sixth electrical signal, adding the sixth electrical signal to the third electrical signal to produce a seventh electrical signal, and integrating the seventh electrical signal on which the detection procedure is performed.

It will thus be seen that the present invention is based on the broad concept of using the second derivative of the composite electrical signal, and more particularly on using both the second and the first derivatives of the composite signal. The method is thus particularly suited for indicating the repetition intervals of the fetal R-waves since the second derivative of the R-waves is hardly affected by baseline changes, nor is the shape affected by heart rate changes, in a normal person so that the detection of the maternal R-wave is of good quality. Best results are obtained when both the second and the first derivatives are used in the manner described above, since a process error which might affect one is not likely to affect the other.

The invention also provides apparatus for performing the above method. The description below describes both a hardware implementation of the apparatus wherein the apparatus includes discrete circuits for performing the various operations, and a software implementation of the apparatus wherein the apparatus includes a microprocessor programmed to perform the various operations.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

A Hardware Implementation (FIGS. 1–4f).

The hardware implementation illustrated in FIGS. 1–3 includes discrete circuits for performing the various operations to be described below, as distinguished from the software implementation to be later described which includes a microprocessor programmed to perform the various operations. Both embodiments are described for detecting the repetition intervals of the fetal R-wave present in a composite, abdominal ECG signal of a pregnant woman, which signal is a composite of both the maternal R-wave and the fetal R-wave, as well as extraneous noise.

Figure 1:
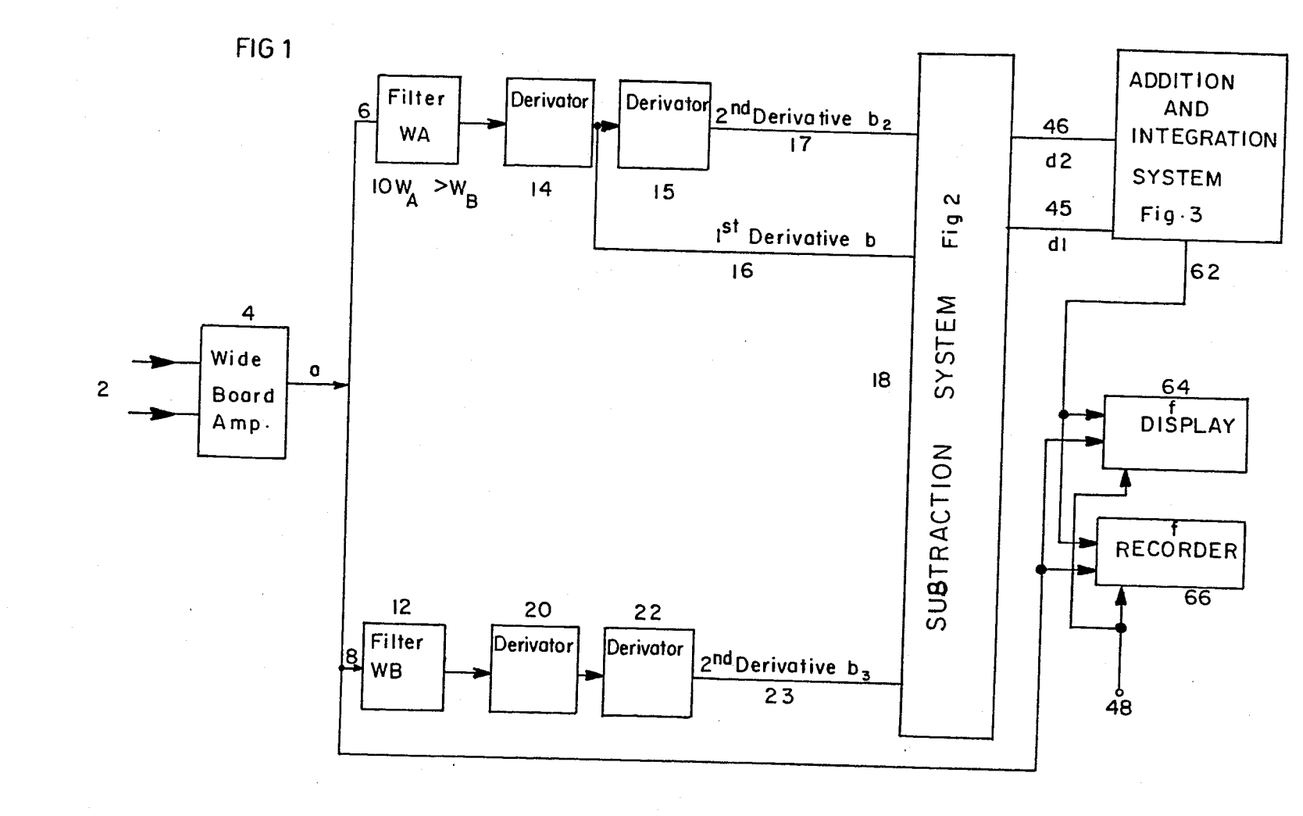
FIG. 1 is a block diagram illustrating a hardware implementation of the invention.
Figure 2:
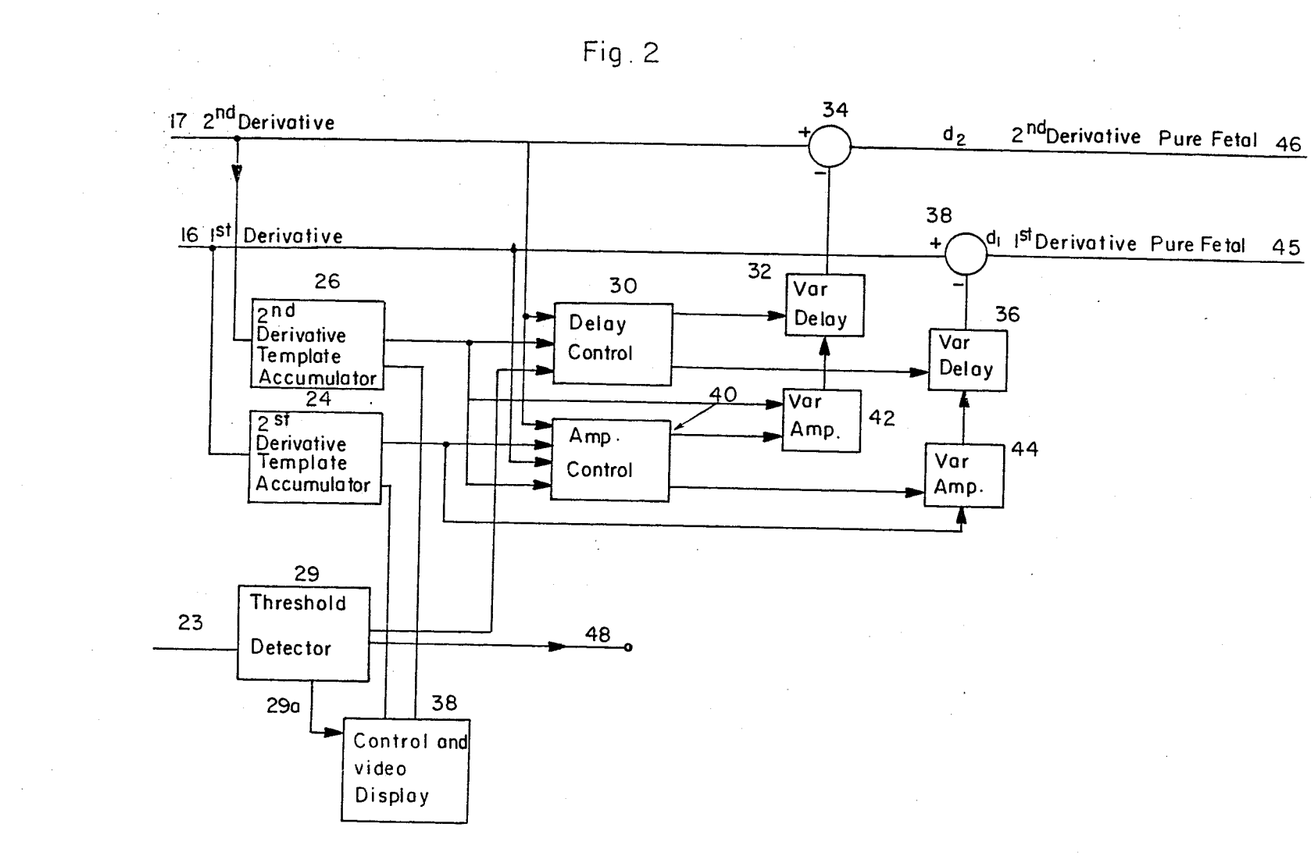
FIG. 2 is a block diagram illustrating the subtraction system in the apparatus of FIG. 1.
Figure 3:
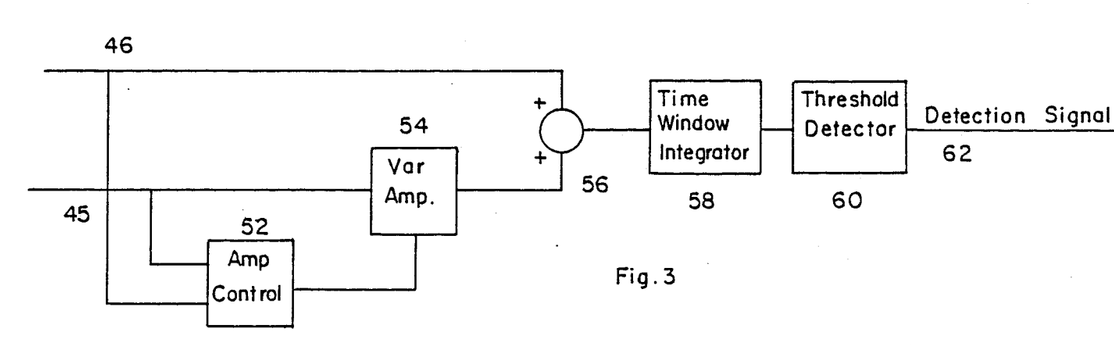
FIG. 3 is a block diagram illustrating the addition and intregration system in the apparatus of FIG. 1.

Thus, the system illustrated in FIGS. 1–3 comprises electrodes, generally designated 2, attachable to the abdominal region of the pregnant woman for detecting the abdominal ECG signal, and a wide band amplifier 4 for amplifying the detected abdominal signal. The amplified abdominal signal is then directed to two distinct channels, 6 and 8, in parallel. Channel 6 includes a filter 10 having a cut-off frequency of between 90–125 (preferably 100) Hz, to pass a composite signal including both the maternal R-wave and the fetal R-wave; whereas channel 8 includes a filter 12 having a cut-off frequency of between 20–30 (preferably 25) Hz, to pass substantially only the maternal R-wave.

Channel 6 further includes a first differential circuit 14 for producing the first derivative of the composite signal including both the maternal and fetal R-waves, and a second differential circuit 15 for producing the second derivative of that composite signal. Both the first and second derivatives are inputted, via lines 16 and 17 resepctively, into a subtraction system, generally designated by block 18. Channel 8 similarly includes a first differential circuit 20 and a second differential circuit 22 for producing the first and second derivatives, respectively, of the original composite signal after the fetal R-wave has been substantially removed by the low cut-off frequency of filter 12, but here only the second derivative signal is inputted into the subtraction system of block 18 via line 23.

FIG. 2 more particularly illustrates the subtraction system of block 18 in FIG. 1.

As shown in FIG. 2, the subtraction system 18 includes two template circuits 24, 26 used for eliminating the maternal R-waves from the abdominal ECG signal. These templates are prepared during an initial Learning period either automatically, or with the aid of an operator control and display unit 28. Unit 28 enables the operator to input data with respect to specified parameters, such as the portion of the maternal R-wave to be processed; this may be selected manually by operating two vertical cursors.

The subtraction system 18 illustrated in FIG. 2 further includes a threshold detector 29 which receives the second derivative of the maternal R-wave from channel 8 via line 23. Threshold detector 29 may carry on automatically, or may be controlled by operator-inputted information via unit 28 and line 29a enabling the operator to select the threshold value, e.g., automatically or, by a horizontal manual cursor, of the maternal R-wave to be processed.

During the Learning period, template circuit 24 averages a plurality of the first derivatives of the composite signal in channel 6, and template circuit 26 accumulates and averages a plurality of the second derivatives of the composite signal in channel 6. This Learning period enables the operator, via control and display unit 28, to establish the time window, namely the vertical cursors, to capture, in template circuits 24 and 26, one maternal R-wave complex of each of the first and second derivatives. Once the operator is satisfied as to the time window established (e.g., by automatically, or vertical cursors via control unit 28) and also as to the threshold level (e.g., automatically, or by horizontal cursors controlling threshold detector 28 via unit 28), the program terminates this Learning period and then proceeds to the actual real-time measurement of the fetal R-wave repetition intervals.

For this purpose, the subtraction system 18 illustrated in FIG. 2 further includes a delay control circuit 30 receiving the second derivative signal from channel 6 and also the second derivative signal from template 26, as well as the output from threshold detector 29. Delay control circuit 30 serves to delay the template signal from circuit 26 relative to the data signal from line 16 so as to match the latter with the template signal by outputting a signal to a variable delay circuit 32 connected to a second-derivative subtractor 34. Delay control circuit 30 outputs a similar signal to variable delay circuit 36 connected to a first-derivative subtrator 38.

The subtraction system 18 illustrated in FIG. 2 further includes an amplitude control circuit 40 which receives both the first-derivative data signals on line 16 and the second-derivative data signals on line 17, as well as the first and second derivative signals from the template circuits 24 and 26, and amplitude matches the template signals to the data signals. Amplitude control circuit 40 thereby controls variable amplification circuit 42 connected to the second derivative subtractor 34, and variable amplification circuit 44 connected to the first derivative subtractor 38.

The first-derivatives subtractor 38 thus receives the data composite signal from line 16, and subtracts from it the signal from the first derivative template 24 after the latter has been time-corrected by circuit 36 and amplitude-corrected by circuit 44. Although template circuit 24 received and averaged the first-derivate composite signals from line 16, because of the time window established by the vertical cursor via the operator control unit 28, its output is substantially restricted to the first derivative of the maternal R-wave. This is subtracted by subtractor 38 from the first-derivative composite signal from line 16, to produce an output signal on line 45 which represents the first derivative of the substantially pure fetal R-wave.

Similarly, the second derivative subtractor 34 receives the second derivative template signal from template circuit 26, after that signal has been time-corrected by circuit 32 and magnitude-corrected by circuit 42, subtracts it from the second derivative composite signal from line 17, and outputs a signal on line 46 which corresponds substantially to the second derivative of the pure fetal R-wave.

Subtractor system 18 illustrated in FIG. 2 includes a further output, on line 48 from the threshold detector 29, representing the presence of a maternal R-wave above the threshold value as preset by the operator via the operator control and display unit 28.

The first and second derivatives of the fetal R-waves, as appearing on lines 45 and 46, respectively, are inputted into the addition and integration system shown by block 50 in FIG. 1, and more particularly illustrated in FIG. 3.

Thus, as shown in FIG. 3, the first-derivative of the fetal R-wave signals on line 45 is first amplification-matched to the second derivative signal on line 46, by amplitude control circuit 52 and variable amplitude circuit 54, and is then added, by adder circuit 56, to the second derivative fetal R-wave signal on line 46. This additional step performed by adder 56 tends to produce a square-wave pulse, which pulse is smoothed by time window integrator 58. The latter pulse is then passed through another threshold detector 60 to remove extraneous noise. The output on line 62 is a substantially square-wave pulse whose leading edge represents the precise location of the fetal R-wave.

As shown in FIG. 1, the square-waves outputted on line 62 is fed with the maternal R-waves outputted on line 48 to a display unit 64. The latter thereby displays the fetal R-waves superimposed over the abdominal ECG signal from line 6. The fetal and maternal R-waves outputted on lines 6 and 62 are also fed to a recorder unit 66 which records the fetal R-waves, the maternal R-waves, and the abdominal ECG.

FIGS. 4a–4f illustrate typical waveforms at various parts of the apparatus of FIGS. 1–3.

Figure 4A:
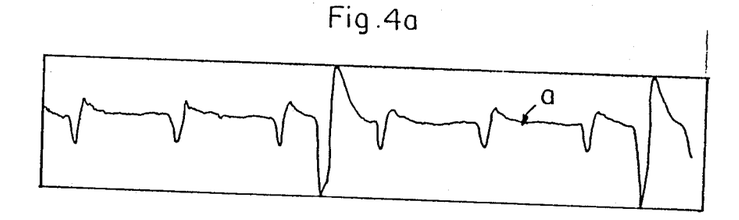
FIGS. 4a–4f illustrate waveforms at various points in the apparatus helpful in understanding its operation.
Figure 4B:
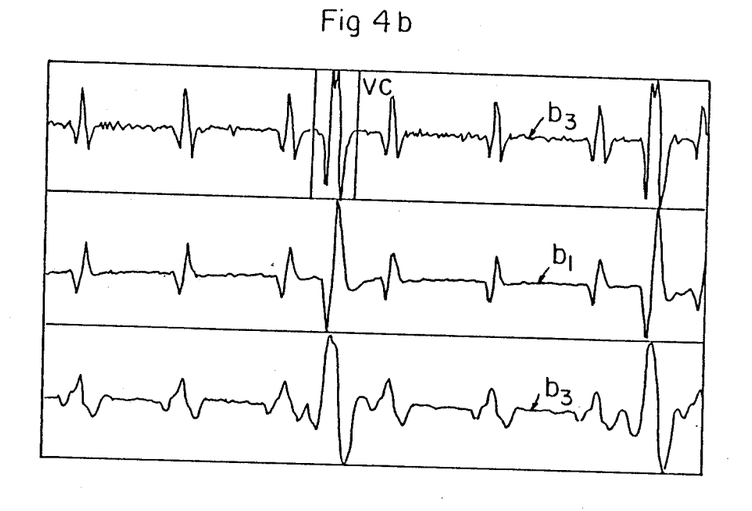
Figure 4C:
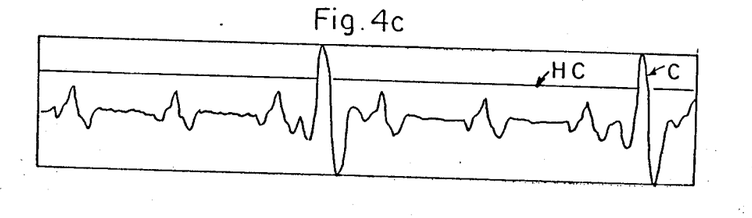
Figure 4D:
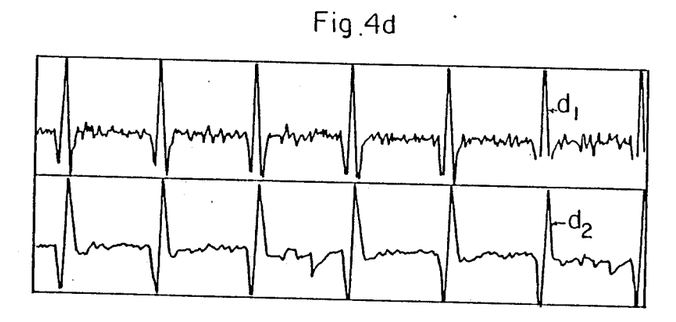
Figure 4E:
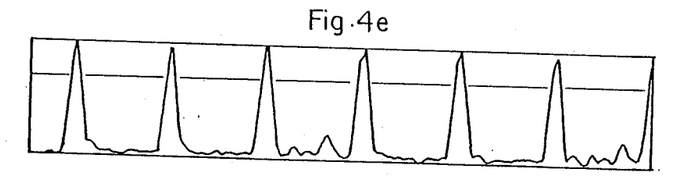
Figure 4F:
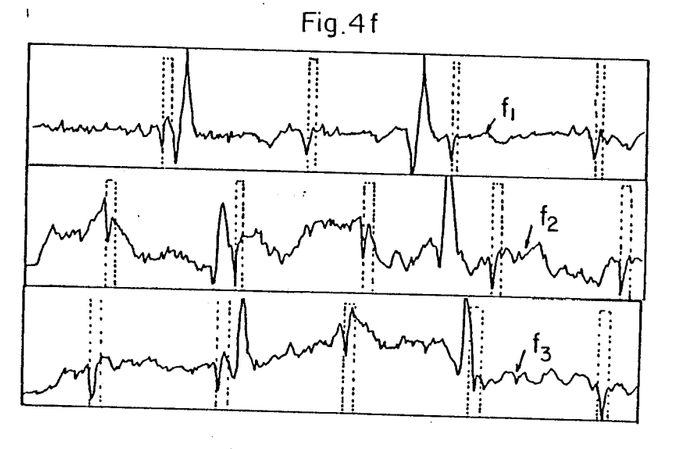

Thus, the waveform of the original ECG signal at point a in FIG. 1 is illustrated in FIG. 4a. FIG. 4b illustrates the waveform at points $b_1$, $b_2$ and $b_3$, respectively, of FIG. 1; FIG. 4c illustrates the waveform at point c in FIG. 2, also showing the horizontal cursor HC for selecting the threshold level; FIG. 4d illustrates the waveforms at points $d_1$ and $d_2$, respectively of FIGS. 1 and 2; FIG. 4e illustrates the waveform at point e of FIG. 3; and FIG. 4f illustrates three examples of waveforms displayed in display unit 64, or recorded in recorder 66, with the repetition intervals of the fetal R-wave, shown in phantom lines, superimposed over the original composite waves, shown in full lines. Waveform $f_1$ in FIG. 4f illustrates a normal example; waveform $f_2$ illustrates a very noisy signal including base-line wander; and waveform $f_3$ illustrates the waveform produced when the maternal R-wave normally hides the fetal R-wave, which would be very difficult, if possible at all, to detect in the previously known procedures.

A Microprocessor Implementation (FIGS. 5–9c)

Figure 5:
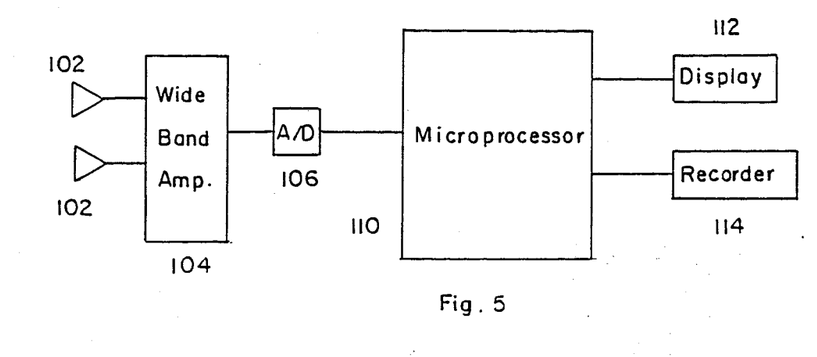
FIG. 5 illustrates a software implementation of the invention.

FIG. 5 illustrates a microprocessor implementation of the novel method, including a microprocessor programmed to perform on-line the above-described operations according to the program illustrated by the flow charts of FIGS. 6–9b.

Thus, the apparatus illustrated in FIG. 5 includes the ECG electrodes 102 for application to the abdominal region of the pregnant woman for detecting the ECG signals comprising a composite of the maternal R-waves and the fetal R-waves. These signals are amplified in wide band amplifier 104 and converted to digital information by analog-to-digital converter 106 before being inputted into the microprocessor 110. The microprocessor processes this information according to the flow charts of FIGS. 6–9b described below, and outputs signals to the display unit 112 and to the recorder unit 114 corresponding to the signals outputted to the display and recorder units 64 and 66, in FIG. 1, displaying the repetition intervals of the fetal R-waves superimposed on the abdominal ECG.

Figure 6:
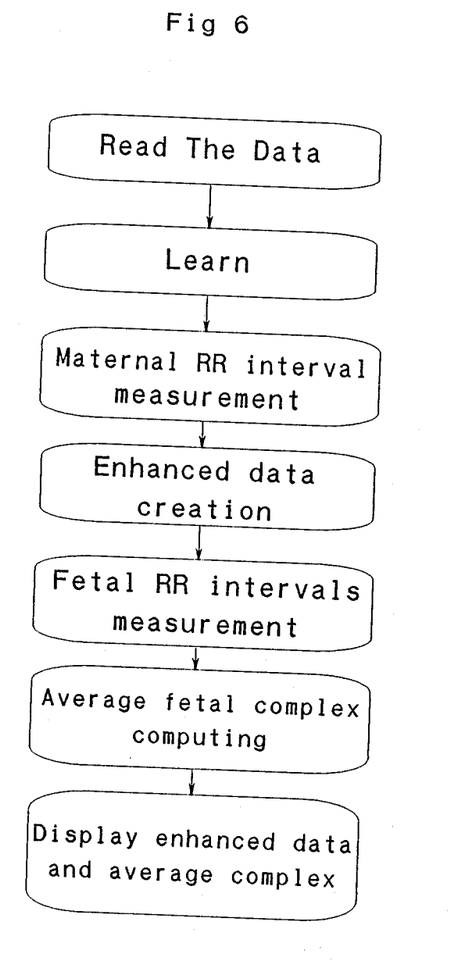
FIG. 6 is a flow chart illustrating the overall operation of the system of FIG. 5.

FIG. 6 is a flow chart illustrating the overall program. As described above with respect to the hardware implementation of FIGS. 1–3, the first part of the program is to Read the Data into the memory and then to execute a Learn procedure to display intermediate results and to obtain automatic or operator's selections and confirmations.

Figure 7A:
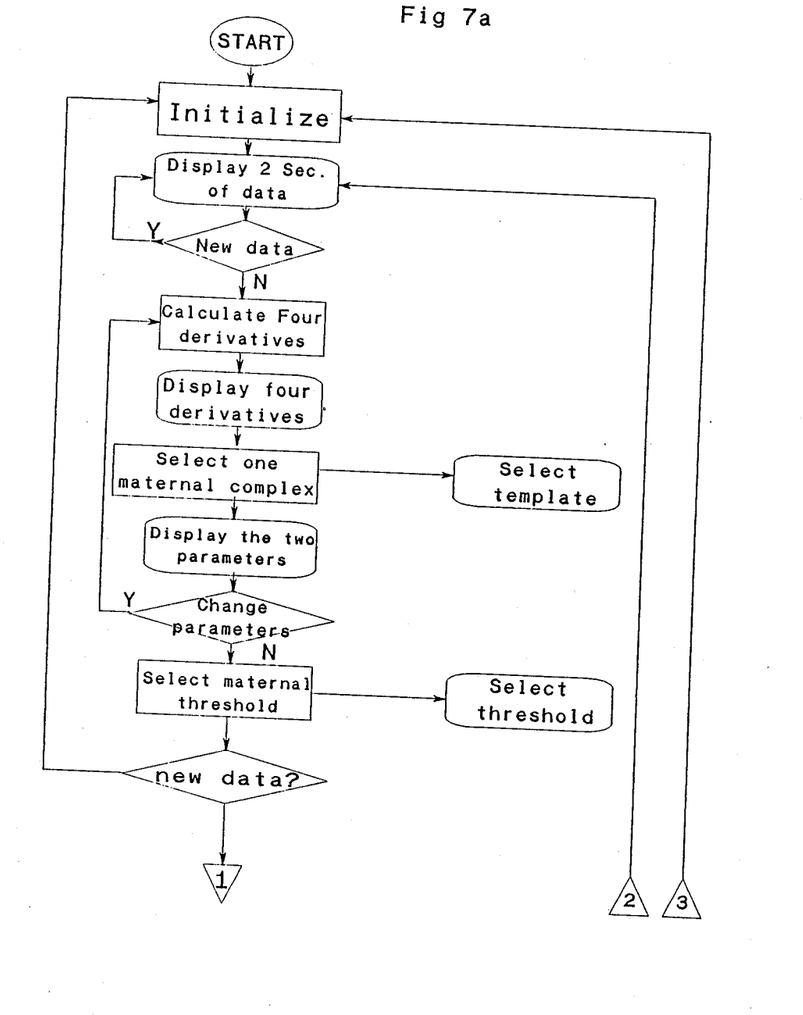
FIGS. 7a, 7b, 7c are flow charts illustrating the Learn procedure in the flow chart of FIG. 6.
Figure 7B:
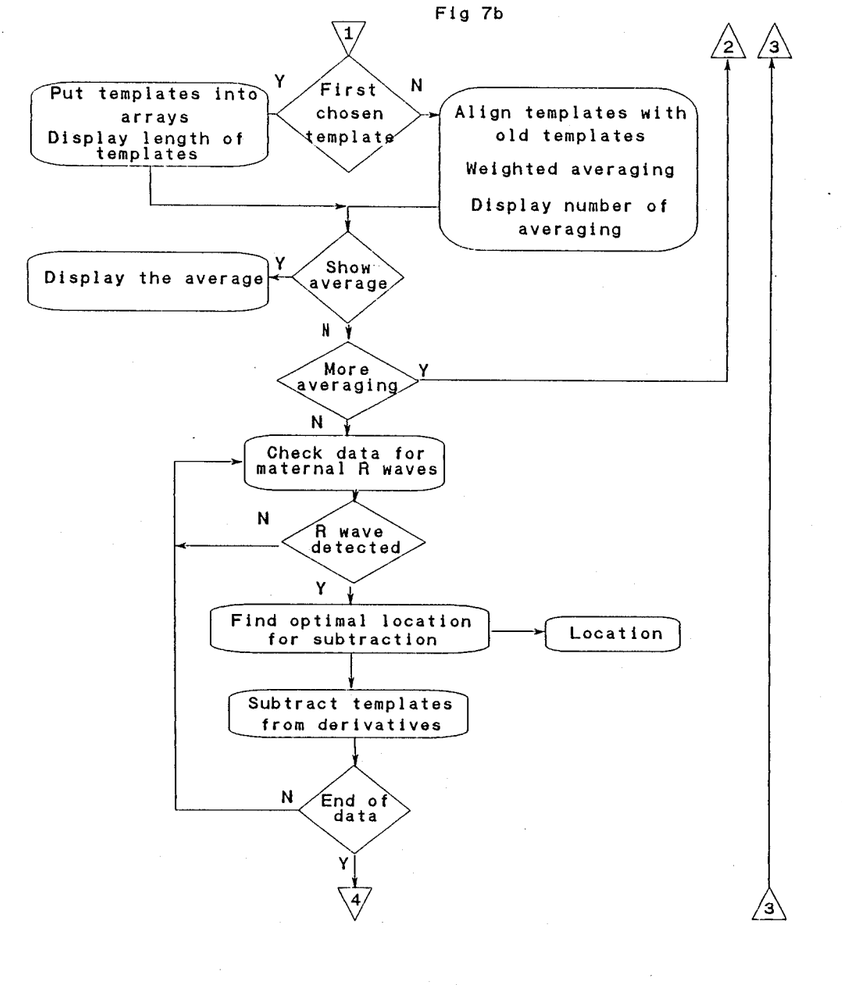
Figure 7C:
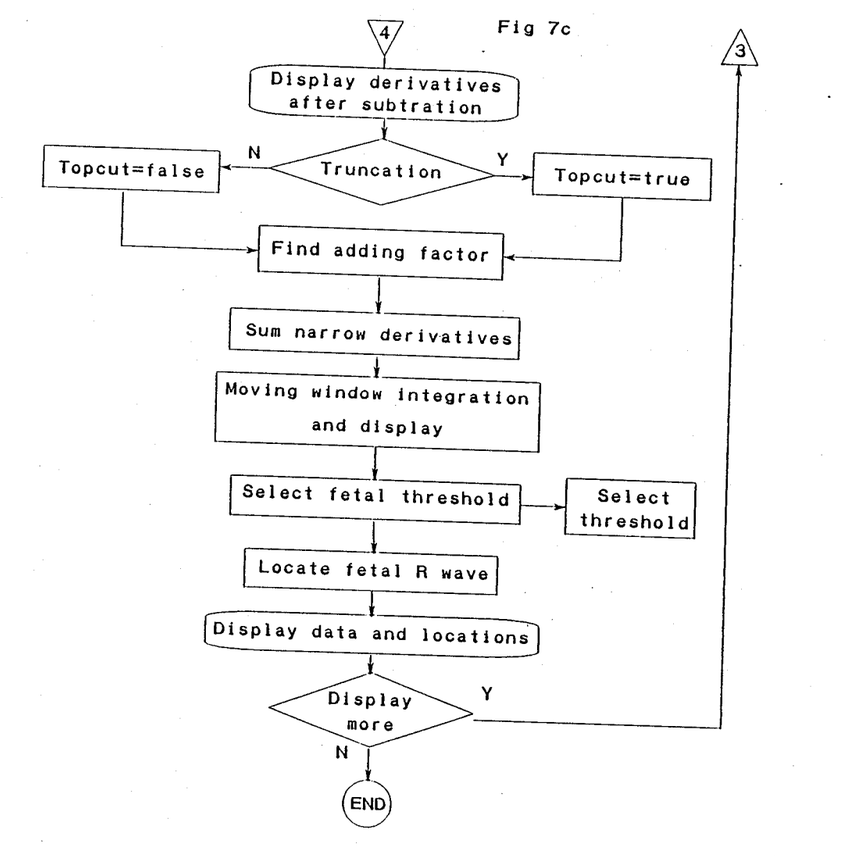

The Learn procedure is more particularly illustrated in the flow charts of FIGS. 7a–7c. In this procedure, all the data is displayed, thresholds are selected either automatically, or on the screen while the data is displayed in the background, and also selection of maternal R-waves is made either automatically, or on the screen. The Learn procedure operates on "chunks" of data of 2-second lengths. For each round, the procedure takes 600 points from the data storage, and calculates the relevant results. The use of these "chunks" enables their display on the screen and the extraction of the data-related parameters from the original data.

As described earlier, the Learn procedure serves two main functions: (1) it helps the operator to confirm or select parameters and templates; and (2) it accumulates templates and parameters, and passes them to the following procedures. The specific manner in which this is accomplished is detailed in the flow charts of FIGS. 7a–7c.

Upon exiting from the Learn procedure, the program enters the Maternal RR Interval Measurement procedure. This procedure is the first of the procedures designed to operate on-line. The data is in the memory of the computer, and from there one sampling point is taken after the other, as if it were taken from the output port of an A/D converter enabling on-line functioning. All data required for computing is preserved in a cyclic array, and only the last 200 sampling points are preserved in order to prevent overloading of the memory.

The Maternal RR Interval Measurement procedure has two objects: (1) it measures the time intervals between all the maternal R-waves in the data, displays them on the screen, and writes on a file if desired by the operator for further use; and (2) it creates a new set of data (enhanced data) by eliminating the maternal R-waves of the original data, leaving the fetal R-waves unchanged.

The maternal RR interval measurement is based on the detection of a maternal R-wave by its second derivative as described above with respect to the hardware implementation of FIGS. 1-3. From the Learn procedure, the threshold for the second "wide" derivative, and the "wide" parameter itself, are obtained. The "wide" parameter derivative responds only to maternal R-waves and not to fetal R-waves.

Figure 8:
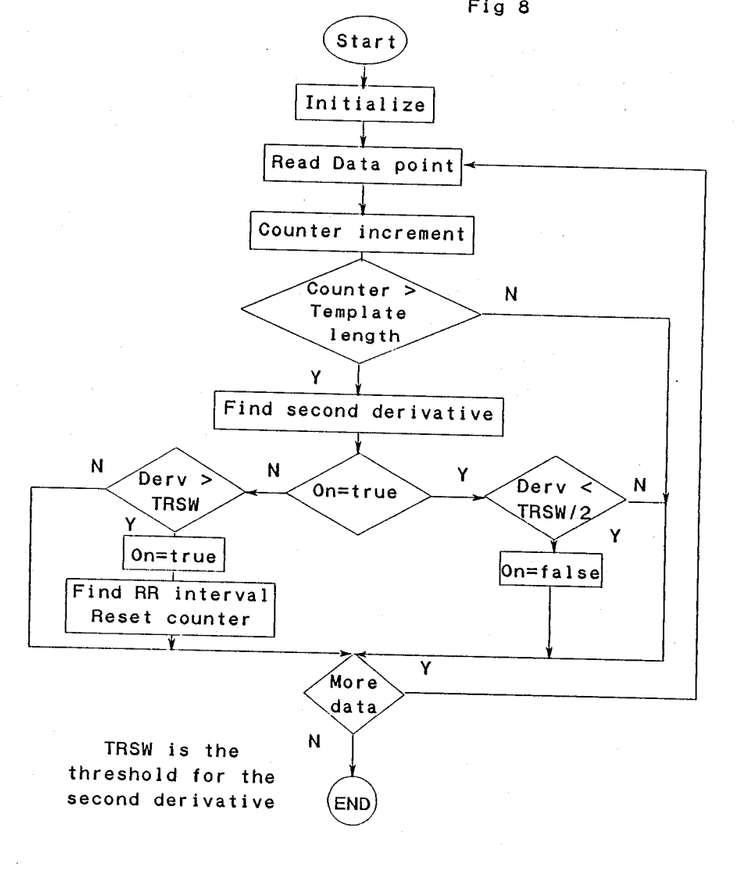
FIG. 8 is a flow chart illustrating the Maternal R-Wave Detection procedure in the flow chart of FIG. 6, FIG. 8a being a timing diagram used in that procedure.

As shown in the flow chart of FIG. 8, the data is scanned for a high (above the threshold) second derivative, and if found, a counter is checked and multiplied by the time scale constant to determine the time measured from the last detected R-wave. A hysteresis loop is used to prevent double detection of the same R-wave. After each detection of a maternal R-wave, the program skips the nearest part of the data in order to save time, and resets the counter.

The computed interval is written on the screen and into the array called MRR (maternal RR intervals). This array may contain, e.g., 4,000 RR intervals. If there are more than 4,000 intervals, an error is detected and execution of the MRR procedure is terminated.

The program then proceeds to the Enhanced Data Creation Procedure. The enhanced data produced in this section of the program is not used for computing procedures but for the human eye only. It reproduces the original data but blanks out the maternal R-waves.

Thus there may be cases when the physician may want to check the fetal heart beats for a single or infrequent phenomena that may be of importance. Events of this kind vanish in the average fetal complex, and the only way to check them is to review the data. Checking the original data is complicated by the presence of the maternal R-waves which limits the resolution of the data display on the screen. Eliminating the maternal R-waves from the data enables plotting the data with the fetal R-waves displayed on the whole screen, giving the physician a more comfortable environment for the scanning task.

The elimination process of maternal complexes is based on the detection of the maternal R-waves. As shown in the timing diagram of FIG. 8a, two factors govern the elimination span: ZSIZE determines the size of the QRS complex, and ZBACK determines the shift from the detection point to the beginning of the complex. Inside that span all values in the cyclic data array are replaced by zero, and then stored in a data structure.

The enhanced data is retrieved from the memory by the display procedure at the end of the program. The same structure is used to store it in a file if it is wanted for future use.

Next illustrated in FIG. 6 is the Fetal RR Intervals Measurement procedure. While the flow chart of FIG. 6 illustrates this as a separate procedure, it can be done at the same time as the Maternal RR Interval Measurement procedure.

The fetal RR Interval Measurement procedure is also performed on-line. Although data is taken from memory and not from the A/D converter, it is taken one sampling point at a time as if from an A/D output. Data and derivatives are stored in 300 terms long cyclic arrays; fetal RR intervals are stored in a 4,000 terms array.

The FRR Interval Measurement procedure has two objects: (1) it measures the time intervals between all the fetal R-waves in the data, displays them on the screen, and writes them in a file in case desired by the operator for future use; and (2) it accumulates all the fetal P-Q-R S-T complexes into a single averaged complex which may reveal some hidden features of the complex.

The fetal RR Intervals Measurement procedure is based on a detection algorithm, which includes the same basic step as described above with respect to FIGS. 1-3, as follows:

1. Use a low-pass filter ("wide" parameter), and a second derivative estimation procedure to detect maternal R-waves:
2. Subtract maternal R-wave traces from "narrow" parameter derivatives; and
3. Use the sum of these first and second derivatives to detect the repetition intervals of the fetal R-waves.

The differentiation and filtration operations are combined in the program into a single operation by time-saving mathematical techniques. The combined procedure is fast and simple, and provides second derivatives along with low-pass filtration. First derivatives are then calculated by recursive integration, saving time and computing power.

Derivatives are required by the detection procedure, and filtration is needed to separate the maternal signal from the recorded abdominal ECG signal. A low-pass filter with a cut-off frequency of about 25 Hz has an output which does not contain traces of the fetal QRS; but a low-pass filter with a cut-off frequency of about 110 Hz transfers both maternal and fetal signals. Consequently, two sets of derivatives are produced, one containing maternal traces only, and the other containing both maternal and fetal traces.

A moving window integration is used to smooth the square wave which is computed as the sum of the first and second derivatives. The size of the integration window is a program constant and is of the same size as a fetal R-wave. Threshold (TRSW) for the integration output is transferred from the Learn procedure, and the fetal R-wave detection is made with it.

Each detection is followed by time calculation of the period from the last R-wave detected, and saving it in the FRR (fetal RR) array, which can be printed out or displayed at the end of the procedure.

In the next procedure, identified in FIG. 6 as the Average Fetal Complex Computing procedure, a plurality of fetal complexes are accumulated and averaged. The importance of an average complex is its ability to reveal hidden qualities of the fetal complex.

The averaging is an equal weight type average; thus, each complex is added to the average complex with the same weight function. All complexes, as detected by the detection portion of the procedure, are included in the average complex.

Figure 9A:
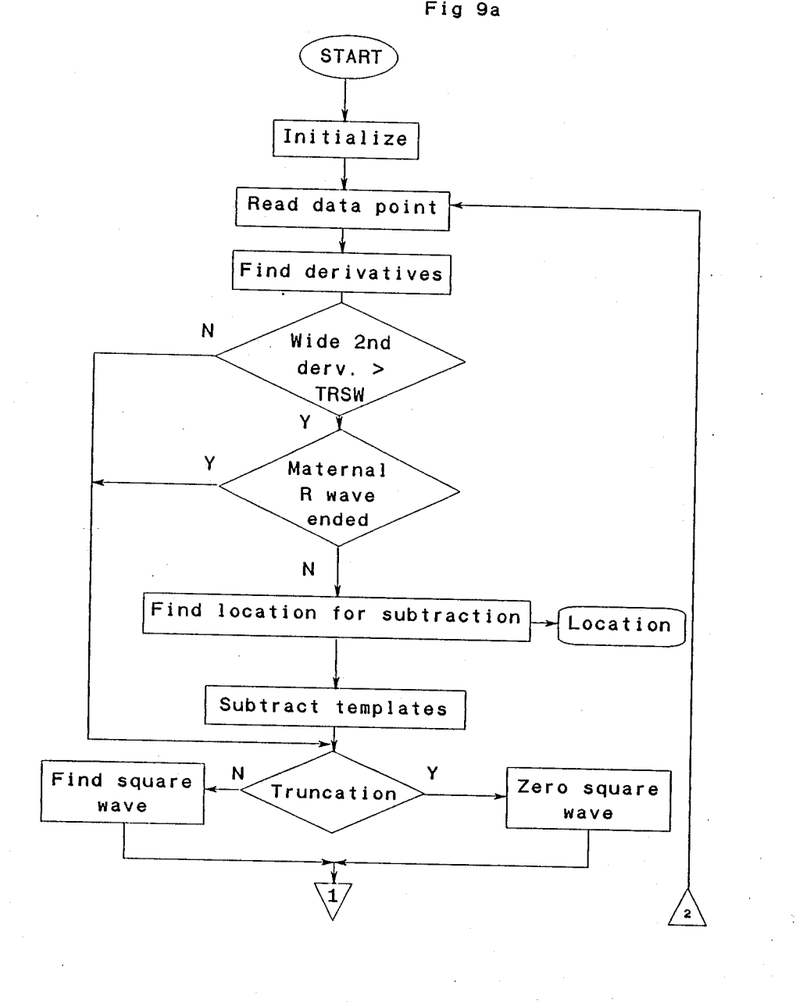
FIGS. 9a and 9b are flow charts illustrating the Fetal R-Wave Interval Measurement procedure in the flow chart of FIG. 6.
Figure 9B:
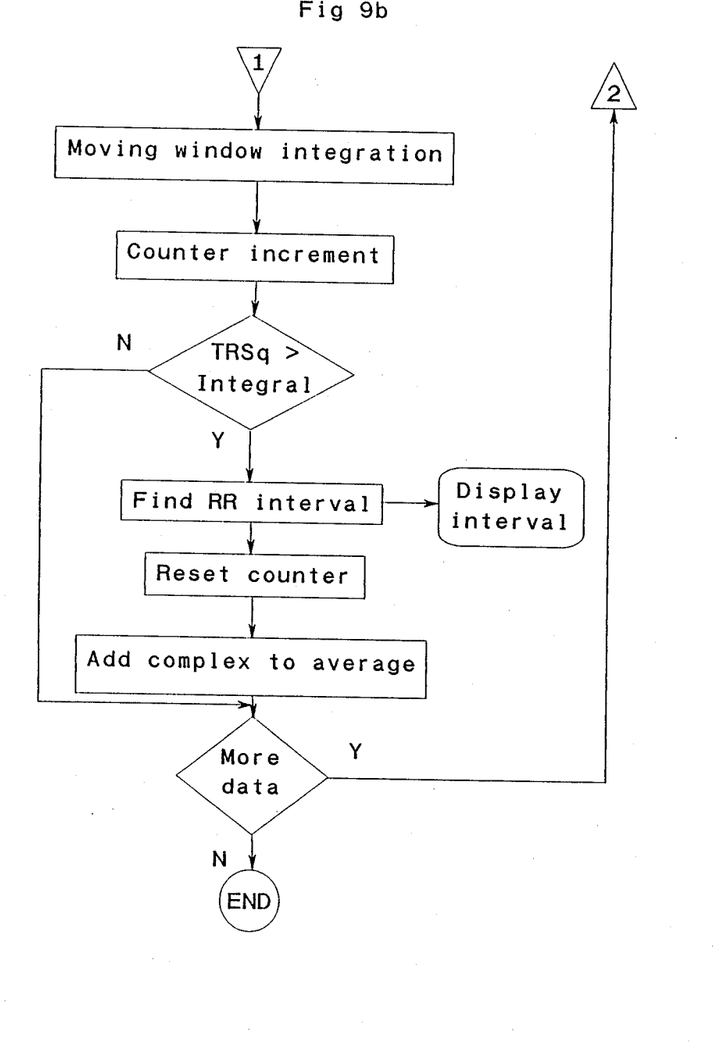
Figure 9C:
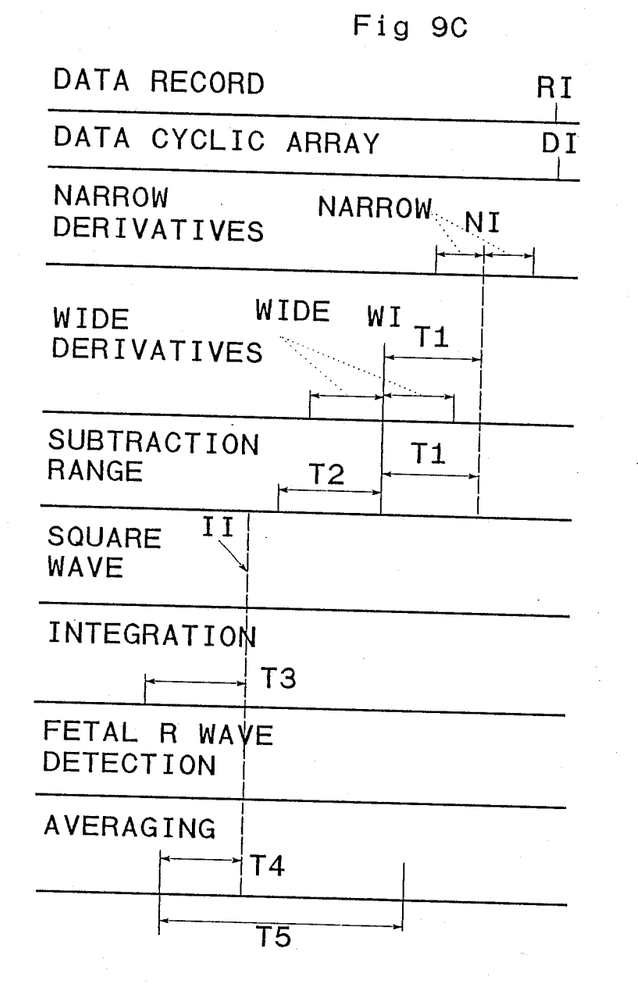
FIG. 9c is a timing diagram used in that procedure.

FIG. 9c illustrates a timing diagram applicable to the procedure, and the following table will be helpful in understanding it:

FRR Timing Table

T1 = MaxSearchR + TemplateLength The limit of the right hand subtraction span.

T2 = MaxSearchL + 1 The limit of the left hand subtraction span.

T3 = IntegralLength The size of the integration window

T4 = AVBack The left limit of the average fetal complex

T5≐AVSize The size of the fetal average complex.
RI The pointer for data reading from the memory.
DI The pointer for data in the cyclic array.
NI The pointer for narrow derivatives computing.
WI The pointer for wide derivatives computing.
II The pointer for integration process.

The size of the average complex (AVSize) and the location of the R-wave with respect to the beginning of the complex (AVBack), are related to the "narrow" parameter of the program, and thus related to the actual length of the fetal complex in each particular case.

The average complex is stored in the AV array. At the end of the procedure, it is possible to save it on a disk file for further use, and to review the average complex using the display procedure of the program.

The averaging procedure used is a very simple procedure. The detection of a fetal R-wave is used as a delayed fiducial point for the averaging.

As shown in FIG. 6, the averaging procedure is followed by a display procedure in which the enhanced data and average complex are displayed. The Display procedure used is "ESHOW", which is a service routine enabling review of the enhanced data and the average fetal complex without saving them on a disk file. This procedure reads the enhanced data from the memory in "chunks" of 2-seconds and plots it on the screen. The operator may "page" along the data and check it for unusual properties. It is possible to review the data again and again without having to store it in a file, before exiting the program.

The second display is the average fetal complex which is plotted once on the screen, after the termination of the enhanced data examination.

At the end of the procedure, the series of accurate beat-to-beat fetal RR-intervals is available for display and print-out, as well as the average fetal complex, the maternal RR-interval series, and the enchanced signal.

While the invention has been described with respect to two preferred embodiments, it will be appreciated that many other variations, modifications, and applications of the invention may be made.

What is claimed is:

1. A method of indicating the repetition intervals of a specified component of a composite cyclically-repeating electrical signal, comprising the steps:
   generating a first electrical signal corresponding to the second derivative of said composite signal;
   generating a second electrical signal corresponding to the second derivative of said composite signal after said specified component has been removed;
   subtracting said second electrical signal from said first electrical signal to produce a third electrical signal;
   and utilizing said third electrical signal for indicating the repetition intervals of said specified component.

2. The method according to claim 1, wherein said second electrical signal is subtracted from said first electrical signal by first preparing a template representing an average of a plurality of cycles of the second electrical signal, and subtracting said template from the first electrical signal.

3. The method according to claim 1, wherein said third electrical signal is utilized for indicating the repetition intervals of said specified component by: generating a fourth electrical signal corresponding to the first derivative of said composite signal, generating a fifth electrical signal corresponding to the first derivative of said composite signal after said specified component has been removed, subtracting said fifth electrical signal from said fourth electrical signal to produce a sixth electrical signal, adding said sixth electrical signal to said third electrical signal to produce a seventh electrical signal, and integrating said seventh electrical signal.

4. The method according to claim 3, wherein said fifth electrical signal is subtracted from said fourth electrical signal by first preparing a second template representing an average of a plurality of cycles of the fifth electrical signal, and subtracting said second template from said fourth electrical signal.

5. The method according to claim 1, including the further step of displaying the repetition intervals of said specified component.

6. The method according to claim 5, including the further step of displaying the composite electrical signal with the repetition intervals of said specified component superimposed thereover.

7. The method according to claim 1, including the further step of recording the repetition intervals of said specified component.

8. The method according to claim 7, including the further step of recording the composite electrical signal with the repetition intervals of said specified component superimposed thereover.

9. The method according to claim 1, wherein said composite electrical signal is an abdominal ECG signal of a pregnant woman including both the maternal R-wave and the fetal R-wave, and said specified component of the composite signal is the fetal R-wave.

10. Apparatus for indicating the repetition intervals of a specified component of a composite cyclically-repeating electrical signal, comprising:
    means for generating a first electrical signal corresponding to the second derivative of said composite signal;
    means for generating a second electrical signal corresponding to the second derivative of said composite signal after said specified component has been removed;
    means for subtracting said second electrical signal from said first electrical signal to produce a third electrical signal;
    and means for utilizing said third electrical signal for indicating the repetition intervals of said specified component.

11. The apparatus according to claim 10, wherein said means for subtracting said second electrical signal from said first electrical signal comprises means for first preparing a template representing an average of a plurality of cycles of the second electrical signal, and means for subtracting said template from the first electrical signal.

12. The apparatus according to claim 10, wherein said means utilizing said third electrical signal for indicating the repetition intervals of said specified component comprises: means for generating a fourth electrical signal corresponding to the first derivative of said composite signal, means for generating a fifth electrical signal corresponding to the first derivative of said composite signal after said specified component has been removed, means for subtracting said fifth electrical signal from said fourth electrical signal to produce a sixth electrical signal, means for adding said sixth electrical signal to said third electrical signal to produce a seventh electrical signal, and means for integrating said seventh electrical signal.

13. The apparatus according to claim 12, wherein said means for subtracting said fifth electrical signal from said fourth electrical signal comprises means for first preparing a second template representing an average of a plurality of cycles of the fifth electrical signal, and means for subtracting said second template from said fourth electrical signal.

14. The apparatus according to claim 13, wherein said means for preparing said two templates comprises a threshold detector to preset the threshold level for the templates.

15. The apparatus according to claim 13, further including amplitute control means for amplitude matching said two templates to said first and fourth electrical signals, respectively; and delay control means for time matching said two templates to said first and fourth electrical signals, respectively.

16. The apparatus according to claim 15, wherein said composite signal is an abdominal ECG signal of a pregnant woman including both the maternal R-wave and the fetal R-wave, and said specified component of the composite is the fetal R-wave; said apparatus further including electrode means for detecting said abdominal ECG signal used for generating said composite signal.

17. The apparatus according to claim 16, wherein said apparatus further includes a first filter receiving said abdominal EGC signal and having a cut-off frequency between 90–125 Hz to pass a composite signal including both the maternal R-wave and the fetal R-wave, which composite signal is used for generating said first and fourth electrical signals; and a second filter, constituting said means for removing the fetal signal, receiving said abdominal ECG signal and having a cut-off frequency between 20–30 Hz to pass substantially only the maternal R-wave, which is used for generating said second and fifth electrical signals.

18. The apparatus according to claim 17, further including display means for displaying the repetition interval of the fetal R-wave superimposed over the maternal R-wave, and recording means for recording the repetition interval of the fetal R-wave superimposed over the maternal R-wave.

19. The apparatus according to claim 10, wherein the apparatus includes discrete circuits for performing the defined operations.

20. The apparatus according to claim 10, wherein the apparatus includes a microprocessor programmed to perform the defined operations.

* * * * *